US011129707B2

(12) United States Patent
Pagnoulle et al.

(10) Patent No.: US 11,129,707 B2
(45) Date of Patent: Sep. 28, 2021

(54) TRIFOCAL INTRAOCULAR LENS WITH EXTENDED RANGE OF VISION AND CORRECTION OF LONGITUDINAL CHROMATIC ABERRATION

(71) Applicant: PhysIOL S.A., Liege (BE)

(72) Inventors: Christophe Robert Marie Armand Pagnoulle, Verviers (BE); Suad Redzovic, Liege (BE); Laure Voisin, Paris (FR); Damien Gatinel, Paris (FR); Jerome Jean D. Loicq, Liege (BE)

(73) Assignee: PhysIOL S.A., Liège (BE)

( * ) Notice: Subject to any disclaimer, the term of this patent is extended or adjusted under 35 U.S.C. 154(b) by 577 days.

(21) Appl. No.: 15/816,726

(22) Filed: Nov. 17, 2017

(65) Prior Publication Data

US 2018/0092739 A1     Apr. 5, 2018

Related U.S. Application Data

(63) Continuation of application No. PCT/EP2016/069230, filed on Aug. 12, 2016.

(30) Foreign Application Priority Data

Aug. 12, 2015  (EP) ..................... 15180752

(51) Int. Cl.
*A61F 2/16*       (2006.01)
*G02B 5/18*       (2006.01)
*G02B 27/42*      (2006.01)

(52) U.S. Cl.
CPC ............ *A61F 2/1618* (2013.01); *A61F 2/164* (2015.04); *A61F 2/1654* (2013.01);
(Continued)

(58) Field of Classification Search
CPC ...... A61F 2/1618; A61F 2/164; A61F 2/1654; G02B 5/1876; G02B 27/4205; G02C 2202/20
See application file for complete search history.

(56) References Cited

U.S. PATENT DOCUMENTS

| 4,210,391 A | 7/1980 | Cohen |
|---|---|---|
| 4,881,804 A | 11/1989 | Cohen |

(Continued)

FOREIGN PATENT DOCUMENTS

| AU | 6922791 A | 7/1991 |
|---|---|---|
| CN | 1042613 A | 5/1990 |

(Continued)

OTHER PUBLICATIONS

International Search Report dated Oct. 28, 2016, for PCT/EP2016/069230, 4 pages.

(Continued)

*Primary Examiner* — Jennifer Dieterle
*Assistant Examiner* — Tiffany P Shipmon
(74) *Attorney, Agent, or Firm* — Dorsey & Whitney LLP

(57) ABSTRACT

Disclosed is an intraocular lens (IOL) including an anterior surface, a posterior surface and an optical axis. At least one of the anterior or posterior surfaces has a diffractive profile formed thereon. The diffractive profile has diffractive focal points for far vision, intermediate vision, and near vision. The diffractive profile corresponds to a superposition of a first partial diffractive profile and a second partial diffractive profile, the first partial diffractive profile has a focal point of order +n that coincides with the diffractive focal point for intermediate vision or with the diffractive focal point for near vision, the second partial diffractive profile has a focal point of order +n that coincides with the diffractive focal (Continued)

point for far vision and a focal point of higher order than +n that coincides with the diffractive focal point for near vision.

28 Claims, 8 Drawing Sheets

(52) U.S. Cl.
CPC ....... *G02B 5/1876* (2013.01); *G02B 27/4205* (2013.01); *G02C 2202/20* (2013.01)

(56) References Cited

U.S. PATENT DOCUMENTS

| | | |
|---|---|---|
| 4,936,666 A | 6/1990 | Futhey |
| 4,995,714 A | 2/1991 | Cohen |
| 5,121,980 A | 6/1992 | Cohen |
| 5,122,903 A | 6/1992 | Aoyama et al. |
| 5,344,447 A | 9/1994 | Swanson |
| 5,699,142 A | 12/1997 | Lee et al. |
| 6,120,148 A | 9/2000 | Fiala et al. |
| 6,951,391 B2 | 10/2005 | Morris et al. |
| 7,025,456 B2 | 4/2006 | Morris et al. |
| 7,232,218 B2 | 6/2007 | Morris et al. |
| 7,441,894 B2 * | 10/2008 | Zhang .................. A61F 2/1654 351/159.44 |
| 7,481,532 B2 | 1/2009 | Hong et al. |
| 7,572,007 B2 | 8/2009 | Simpson |
| 8,100,527 B2 | 1/2012 | Hong et al. |
| 8,636,796 B2 | 1/2014 | Houbrechts et al. |
| 8,652,205 B2 | 2/2014 | Hong et al. |
| 9,223,148 B2 | 12/2015 | Fiala et al. |
| 9,320,594 B2 | 4/2016 | Scwiegerling |
| 9,335,563 B2 | 5/2016 | Weeber |
| 10,197,815 B2 | 2/2019 | Weeber |
| 2006/0055883 A1 | 3/2006 | Morris et al. |
| 2006/0098162 A1 | 5/2006 | Bandhauer et al. |
| 2006/0098163 A1 | 5/2006 | Bandhauer et al. |
| 2006/0116764 A1 | 6/2006 | Simpson |
| 2007/0182924 A1 | 8/2007 | Hong et al. |
| 2008/0300679 A1 | 12/2008 | Altmann |
| 2009/0088840 A1 | 4/2009 | Simpson et al. |
| 2009/0122262 A1 | 5/2009 | Hong et al. |
| 2011/0267693 A1 | 11/2011 | Kobayashi et al. |
| 2012/0140166 A1 * | 6/2012 | Zhao .................. A61F 2/1618 351/159.15 |
| 2014/0009736 A1 | 1/2014 | Zhao et al. |
| 2019/0171036 A1 | 6/2019 | Weeber |

FOREIGN PATENT DOCUMENTS

| | | |
|---|---|---|
| CN | 101118315 A | 2/2008 |
| CN | 101172057 A | 5/2008 |
| CN | 101416096 A | 4/2009 |
| CN | 101416097 A | 4/2009 |
| CN | 101422392 A | 5/2009 |
| CN | 101686856 A | 3/2010 |
| CN | 102762169 A | 10/2012 |
| CN | 102947749 A | 2/2013 |
| CN | 104127263 A | 11/2014 |
| CN | 104755012 A | 7/2015 |
| CN | 104783925 A | 7/2015 |
| EP | 64812 A2 | 11/1982 |
| EP | 0064812 B1 | 8/1985 |
| EP | 343067 A1 | 11/1989 |
| EP | 375291 A2 | 6/1990 |
| EP | 0375291 B1 | 3/1997 |
| EP | 0888564 B1 | 9/2002 |
| EP | 1279992 A2 | 1/2003 |
| EP | 1884219 A2 | 2/2008 |
| EP | 1891912 A1 | 2/2008 |
| EP | 2045648 A1 | 4/2009 |
| EP | 2290411 A1 | 3/2011 |
| EP | 2377493 A1 | 10/2011 |
| EP | 2378319 A1 | 10/2011 |
| EP | 2503962 A1 | 10/2012 |
| IE | 68759 B1 | 7/1996 |
| JP | 08-507158 A | 7/1996 |
| JP | 2000-511299 A | 8/2000 |
| JP | 2006-139246 A | 6/2006 |
| JP | 2010-158315 A | 7/2010 |
| JP | 4551489 B2 | 9/2010 |
| RU | 2303961 C1 | 8/2007 |
| RU | 2482817 C2 | 5/2013 |
| WO | 94/11765 A1 | 5/1994 |
| WO | 94/17435 A1 | 8/1994 |
| WO | 9744689 A1 | 11/1997 |
| WO | 01/04667 A1 | 1/2001 |
| WO | 2006023404 A2 | 3/2006 |
| WO | 2006/060480 A2 | 6/2006 |
| WO | 2006/063994 A1 | 6/2006 |
| WO | 2007/092949 A1 | 8/2007 |
| WO | 2010/079528 A1 | 7/2010 |
| WO | 2010/079537 A1 | 7/2010 |
| WO | 2010/093975 A2 | 8/2010 |
| WO | 2011/092169 A1 | 9/2011 |
| WO | 2014/033543 A2 | 3/2014 |
| WO | 2014111831 A1 | 7/2014 |

OTHER PUBLICATIONS

Written Opinion dated Oct. 28, 2016, for PCT/EP2016/069230, 7 pages.
Jorge Albero et al., Generalized diffractive optical elements with asymmetric harmonic response and phase control, Applied Optics / vol. 52, No. 15 / 20, May 2013, pp. 3637-3644.

* cited by examiner

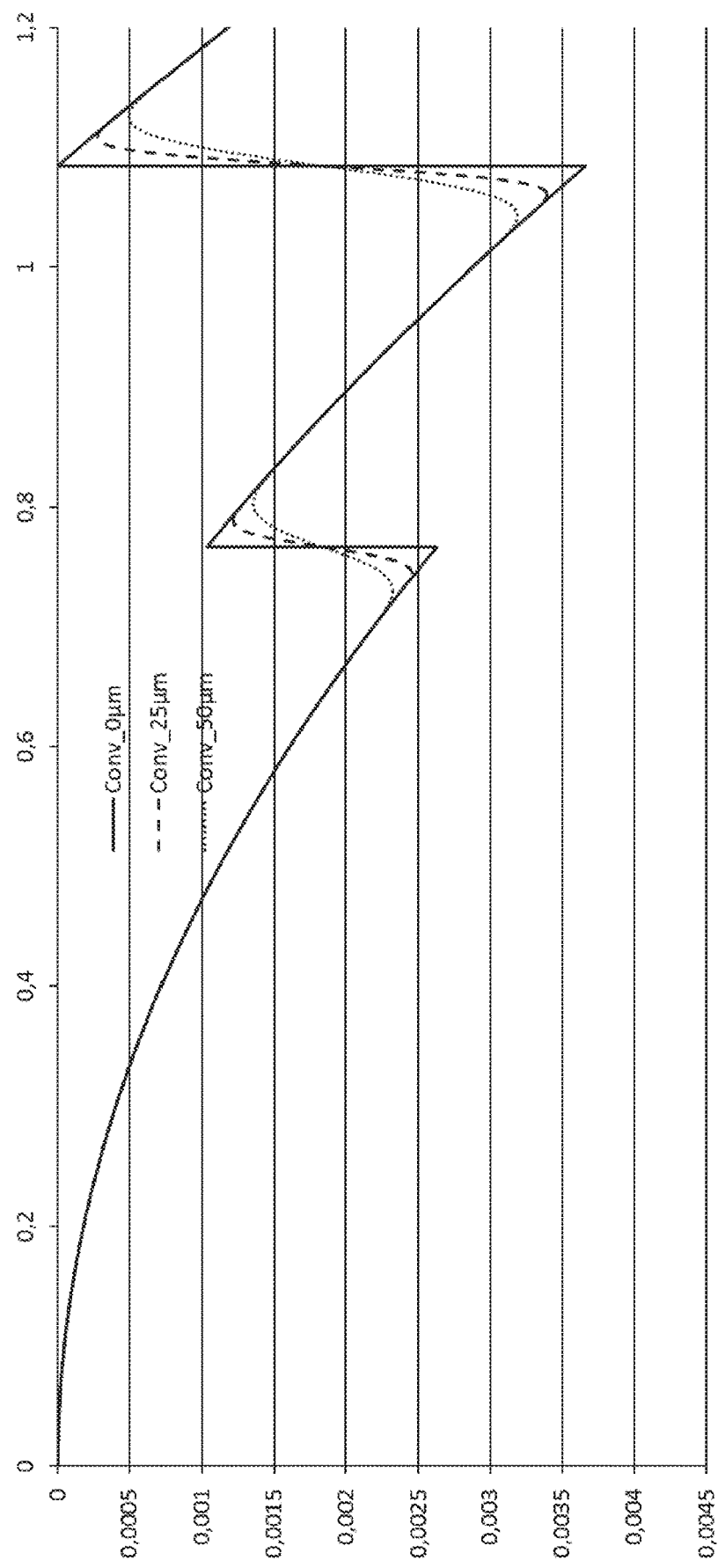

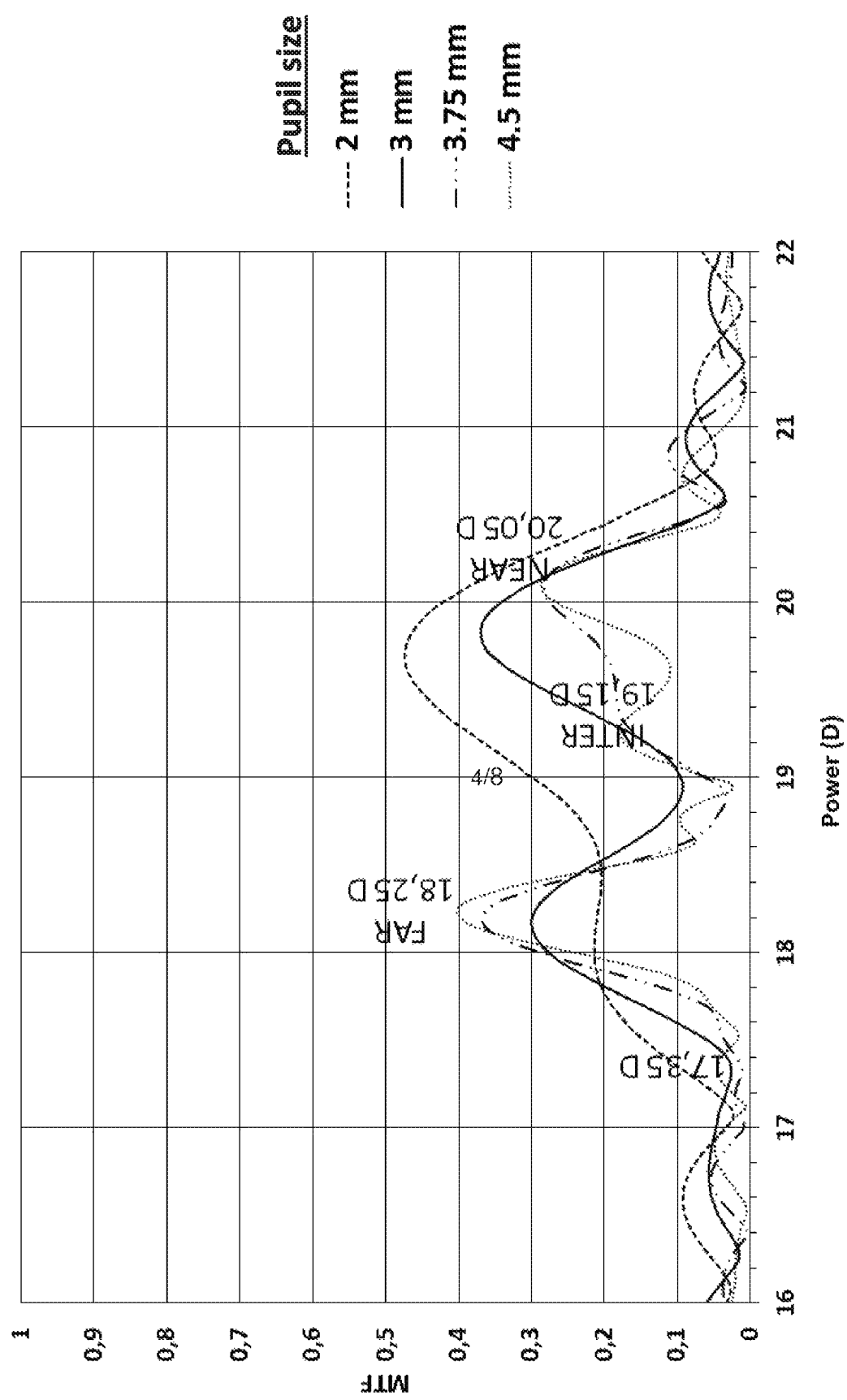

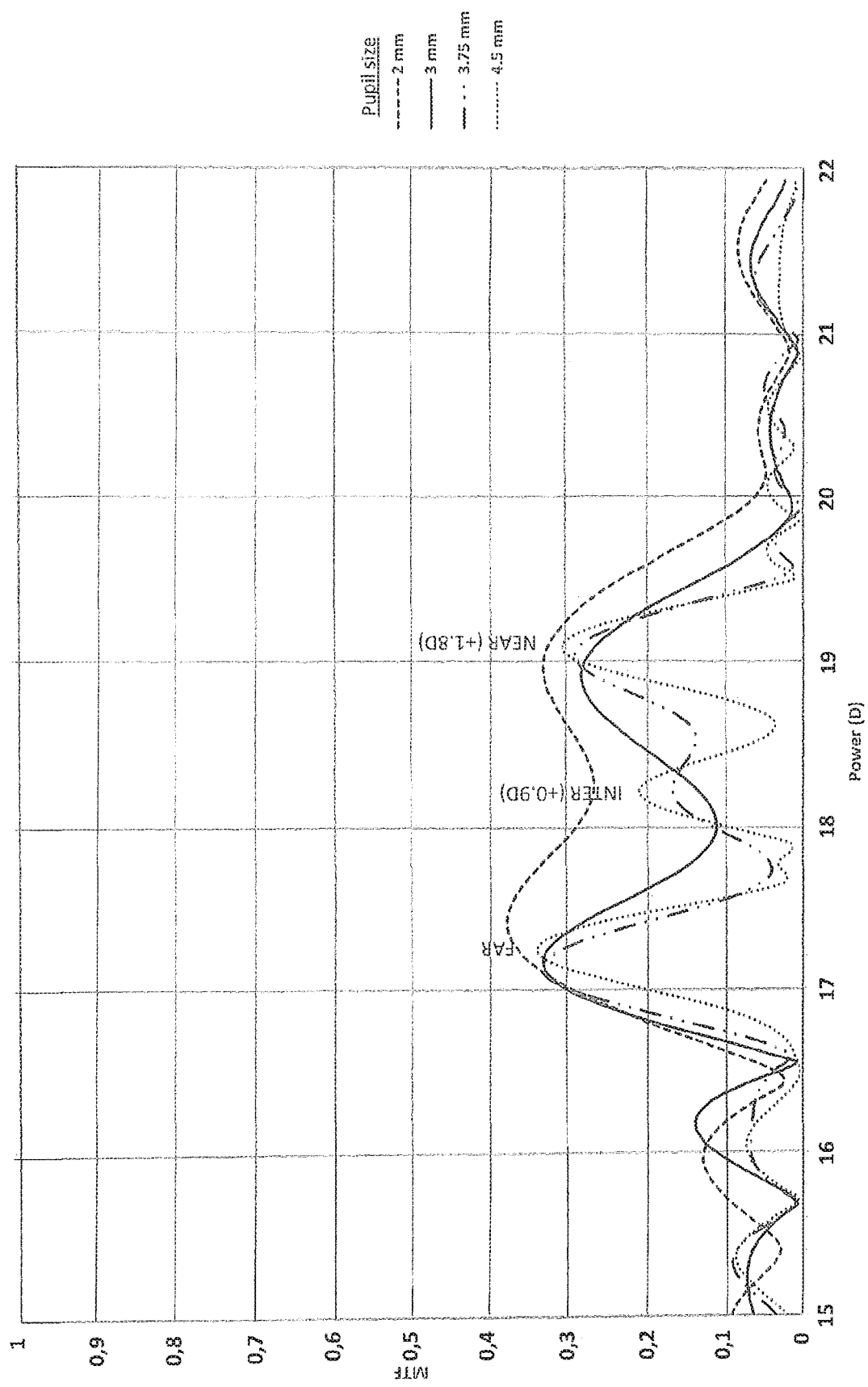

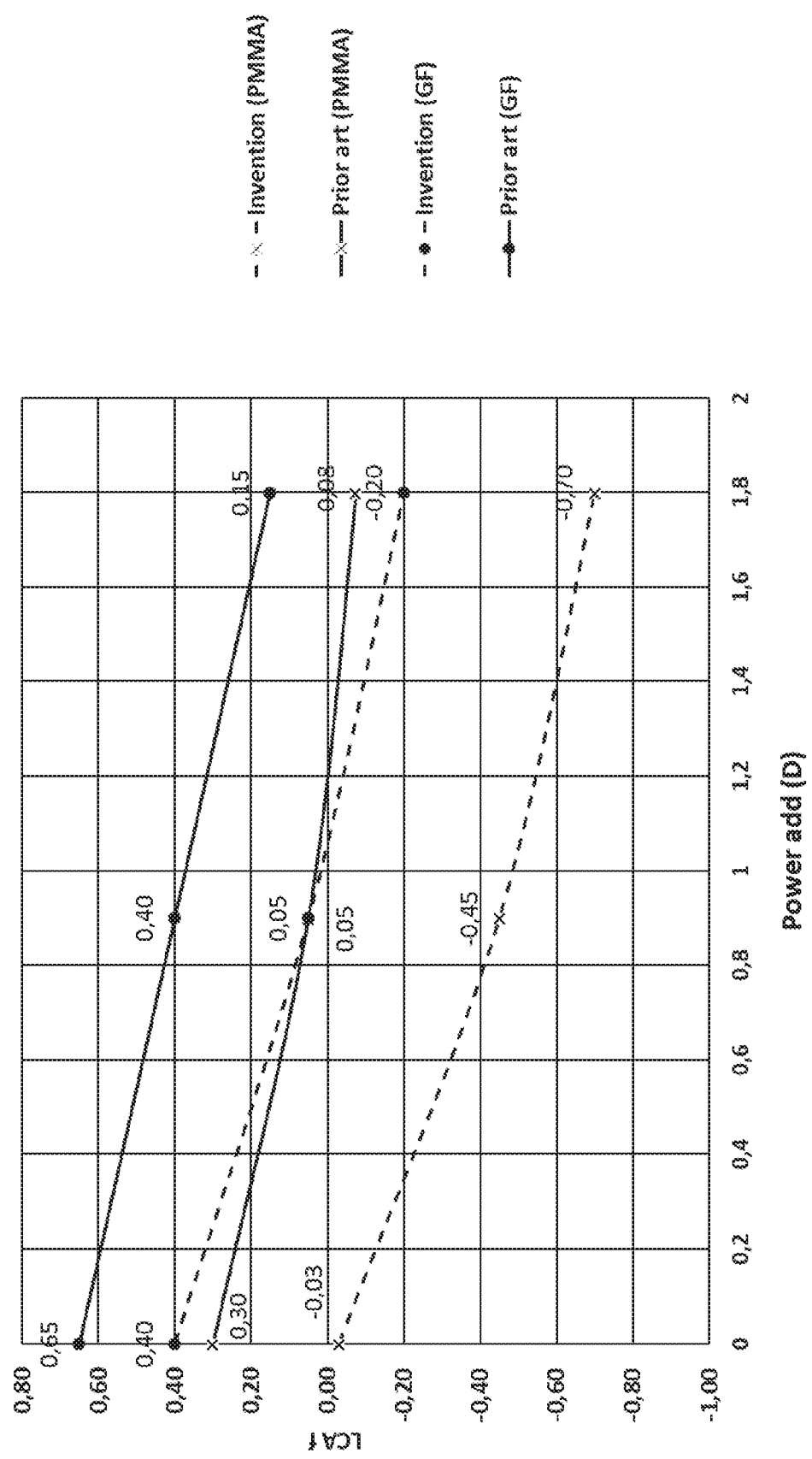

TRIFOCAL INTRAOCULAR LENS WITH EXTENDED RANGE OF VISION AND CORRECTION OF LONGITUDINAL CHROMATIC ABERRATION

CROSS-REFERENCE TO RELATED APPLICATIONS

This application is a continuation of PCT Patent Application No. PCT/EP2016/069230, filed Aug. 12, 2016, entitled "Trifocal Intraocular Lens with Extended Range of Vision and Correction of Longitudinal Chromatic Aberration," which claims priority to European Application No. 15180752.6, filed Aug. 12, 2015, entitled "Trifoal Intraocular Lens with Extended Range of Vision and Correction of Longitudinal Chromatic Aberration," the contents of both of which are hereby incorporated by reference in their entirety.

FIELD

The present invention relates to an intraocular lens, and in particular to an intraocular lens with three focal points and a diffractive profile on an anterior or posterior face. This lens provides extended range of vision (EROV) from far to near distance and reduces linear chromatic aberration (LCA).

BACKGROUND

An intraocular lens (IOL) is a lens which may be implanted in the eye, most often for replacing the crystalline lens after a cataract operation. It normally includes lateral flexible supports, so-called "haptics", used for supporting the lens in the capsular bag. An intraocular lens may be a refractive lens, a diffractive lens, or a refractive-diffractive lens. A refractive lens converges light towards a focal point on the optical axis by refraction, which refractive focal point may also be referred to as a diffractive focal point of zeroth order. A diffractive lens creates a diffraction pattern forming one focal point on the optical axis per diffraction order distinct from zeroth order. Simply put, a focal point of n-th order is characterized by constructive interference of light waves having a phase difference of multiples of n wavelengths. A refractive-diffractive lens combines the features of both of them.

The crystalline lens has some flexibility allowing, through the action of ciliary muscles, adaptation of the eye to far or near vision. By pulling on the edges of the crystalline lens, the ciliary muscles flatten it, thereby displacing its focal point. However, because of weakening of the ciliary muscles due to age, or because of the replacement of the crystalline lens with an intraocular lens, a patient may at least partly lose this adaptability. In order to address this problem, several types of bi- or multi-focal intraocular lenses have been proposed.

Monofocal IOLs are intended to provide vision correction at one distance only, usually the far focus. Since a monofocal IOL provides vision treatment at only one distance and since the typical correction is for far distance, spectacles are usually needed for good near vision and sometimes for intermediate vision. Bi- or multi-focal refractive intraocular lenses having variable refractive power, normally decreasing from the center of the lens towards an outer edge, are known from prior art. Such intraocular lenses are e.g. sold under the brands lolab® NuVue®, Storz® Tru Vista®, Alcon® AcuraSee®, Ioptex®, Occulentis M Plus and AMO® ReZoom®. This design takes advantage of the fact that in situations where near vision is required, such as for example for reading, one normally has high luminosity, which causes closing of the iris, concealing the outer portion of the lens and allowing light to only pass through the more central portion having the highest refractive power. In some cases, the refractive intraocular lens may have an aspherical profile, so as to partly or totally correct the aspherical aberration of the cornea and to thereby improve the contrast sensitivity of the pseudophakic eye, i.e. the eye implanted with the intraocular lens.

These purely refractive bi- or multi-focal lenses however have certain drawbacks. One problem is that their behavior is strongly dependent on the size of the pupil. Further, because they have several focal points, they only provide reduced contrast and may form halos, in particular, in far vision, with reduced luminosity.

In addition, so-called "refractive-diffractive" intraocular lenses are known in the field. Typically, these lenses provide a refractive optical focal point (which according to the terminology used herein corresponds to the focus of "zeroth diffraction order") for far vision, and at least one diffractive focal point of first order for near vision. Certain refractive-diffractive intraocular lenses, such as for example those developed by 3M® and those developed by AMO® and distributed under the brand of Tecnis® share the light in a substantially equal fraction between both of these two focal points. On the other hand, the intraocular lenses Acri.Tec® Acri.LISA® 366D exhibit an asymmetrical distribution of the light, with more light directed towards the focal point for far vision than for the focal point for near vision, with the aim of improving the contrast and reducing the formation of halos in far vision.

In the article "History and development of the apodized diffractive intraocular lens", by J. A. Davison and M. J. Simpson, J. Cataract Refract. Surg. Vol. 32, 2006, pp. 849-858, a refractive-diffractive intraocular lens is described in which the diffractive profile is apodized, having a profile height that decreases with increasing distance from the optical axis. This lens, sold by Alcon® under the brand ReSTOR®, thereby allows a variation of the distribution of the light between the focal points for far vision and near vision according to the aperture of the pupil.

These refractive-diffractive intraocular lenses of the state of the art, however, also have certain drawbacks. Notably, they are almost purely bifocal, with a spacing between the focal point for far vision and the one for near vision such that they may be uncomfortable in intermediate vision.

Multi-focal refractive-diffractive lenses having at least one intermediate focal point have also been proposed. In International Patent Application WO 94/11765, a refractive-diffractive lens is proposed with a focal point of order zero for intermediate vision, a focal point of order +1 for near vision, and a focal point of order −1 for far vision. This lens, however, only allows a substantially equal distribution of the light between the three focal points, and in particular only allows an equal distribution of light between the near and the far focus, independently of the pupil aperture.

In International Patent Application WO 2007/092949, an intraocular lens is proposed including a plurality of diffractive profiles, each with a distinct focal point of order +1. The different profiles are arranged on distinct concentric areas of the IOL optical portion, and the distribution of the light between the focal points will therefore strongly depend on the pupil size, in the same way as known from the refractive multi-focal intraocular lenses referred to above. For instance, the number of focal points would change with pupil aperture, i.e. the lens is bifocal at small pupil sizes, the third focal point being effective only upon pupil enlargement.

Further, almost all the diffractive and refractive-diffractive intraocular lenses of the state of the art have the drawback of losing a considerable portion of the light towards unusable focal points of an order greater than +1.

WO2011/092169 (referred to as WO'169 in the following) describes an intraocular lens providing for three useful focal points with a distribution of the light between the three focal points which does not necessarily depend on the pupil size. Said lens virtually displays two superposed partial diffractive profiles in order to obtain two different focal points of order +1 assigned, for example, to near and intermediate visions, respectively, while the zeroth order of the combined profile (i.e. the superposition of the first and second partial profiles) is dedicated to the far vision. Thus, this lens has two useful diffractive focal points and one useful refractive focal point. A remarkable advantage of the IOL of WO'169 is that it limits the light losses due to diffraction orders greater than +1. For this, the diffraction focal point of order +1 of the first partial profile may also substantially coincide on the optical axis with a focal point of higher order than +1, e.g. +2, associated with the second partial diffractive profile. Thus, the light directed towards said focal point of this higher order of the second partial profile is not lost, but is used for reinforcing the focal point of order +1 of the first partial profile, typically the focal point for near vision.

Although the above trifocal lens leads to improved quality of vision for many patients, particularly for the vision at intermediate distance, additional improvements would be beneficial. In particular, the reduction of the longitudinal chromatic aberration (LCA) can be beneficial for the quality of vision. In the particular case of a multifocal lens and in the case where the LCA reduction would concern the plurality of foci, a patient could benefit of enhanced image quality across a wide and extended range of distances.

Standard bifocal lens designs partition the light between the diffractive order zero and the order +1 providing far power and add power for closer distance, respectively. Such bifocal lenses may not sufficiently correct or treat chromatic aberration, particularly in the far focus. WO 2014/033543 describes a diffractive bifocal intraocular lens suitable for directing the light toward the order +1 and the order +2, the order 0 being inactivated or at least being insufficient for providing useful focal point. Such a lens is commercially available under the brand of Tecnis Symfony® and is reported to reduce or to correct the chromatic aberration of the phakic eye for the two foci, i.e. the focus for far vision as provided by the order +1 and the focus for near vision as provided by the order +2.

SUMMARY

The problem underlying the invention is to provide an intraocular lens that provides for an extended range of vision but, at the same time avoids vision impairment due to longitudinal chromatic aberration.

This object is solved by an intraocular lens (IOL) according to claim 1. Preferable further developments are defined in the dependent claims.

The IOL of the invention includes an anterior surface, a posterior surface and an optical axis. On at least one of the anterior or posterior surfaces, a diffractive profile is formed, said diffractive profile providing for
 a diffractive focal point for far vision,
 a diffractive focal point for intermediate vision, and
 a diffractive focal point for near vision.

The diffractive profile corresponds to a superposition of a first partial diffractive profile and a second partial diffractive profile, wherein
 the first partial diffractive profile has a focal point of order +n that coincides with the diffractive focal point for intermediate vision or with the diffractive focal point for near vision,
 the second partial diffractive profile has a focal point of order +n that coincides with the diffractive focal point for far vision, and
 a focal point of higher order than +n of the second partial diffractive profile coincides with the diffractive focal point for near vision.

Herein, each of the first and second partial diffractive profiles has plural steps with corresponding step heights, said step heights fulfilling the following condition in at least a portion of said diffractive profile: $n < a_1 + a_2 < n+1$, wherein:

$$a_1 = \overline{h_1} / \left( \frac{\lambda}{|n_2 - n_1|} \right),$$

$$a_2 = \overline{h_2} / \left( \frac{\lambda}{|n_2 - n_1|} \right),$$

$\overline{h_1}$ is the average height of the steps of the first partial diffractive profile in said portion of the diffractive profile,
 $\overline{h_2}$ is the average height of the steps of the second partial diffractive profile in said portion of the diffractive profile,
 $\lambda = 550$ nm,
 $n_2$ is the refractive index of the lens material,
 $n_1 = 1.3345$, and
 $n = 1$ or 2

Herein, $n_1$ resembles the refractive index of the implantation medium, which is assumed to amount to 1.3345.

Moreover, the feature that certain step height conditions shall apply "in at least a portion of said diffractive profile" indicates that the condition may apply in the entire diffractive profile, or just in a portion thereof. Also, the fact that the diffractive profile of the invention is formed on at least one of the anterior or posterior surfaces does of course not exclude that other profiles are formed on other regions of said IOL. However, in the embodiments shown below, the diffractive profile according to the invention extends essentially over the entire effective area of the IOL even at large pupil openings of e.g. 4.5 mm.

Accordingly, the IOL of the present invention has three diffractive focal points, whereas the IOL of WO'169 has two diffractive focal points only, namely diffractive focal points for near and intermediate vision, while the focal point for far vision is refractive focal point. The advantage of an IOL with only diffractive focal points is that the longitudinal chromatic aberration (LCA) can be decreased. LCA is a phenomenon according to which light of different wavelengths is focused at different positions along the optical axis. In a refractive lens, the LCA is due to a wavelength-dependency of the index of refraction. For most materials, the index of refraction increases with decreasing wavelength, which means that the refractive focal power of the refractive lens becomes higher for shorter wavelengths.

Diffractive optical elements, on the other hand, suffer from LCA too, but the effect is opposite: the longer the wavelength, the higher the optical power (or in other words, the shorter the focal length). This means that in a lens which provides for both, refractive and diffractive optical power, the two opposite effects may at least partly cancel out, so that in total, the chromatic aberration can be significantly reduced. Although the IOL of the invention does not have a significant refractive focal point, it nevertheless does have refractive power and hence exhibits a corresponding contribution to the LCA. Then, if the IOL has a diffractive focal point for far vision, as is the case for the present invention, the LCA as effected by the refractive power of the IOL can already be at least partially compensated at the focal point for far vision. This is particularly important, because far vision is often necessary under weak light conditions, such that LCA becomes particularly disturbing.

Surprisingly, by properly choosing the parameters $a_1$ and $a_2$ as defined above, a very useful trifocal IOL with purely diffractive focal points can be obtained, as will be demonstrated in more detail below, which allows to significantly reduce the adverse effects of LCA. At the same time, since the IOL provides for three focal points, it exhibits a favorable extended range of vision, as will be likewise demonstrated below. A further advantage of the IOL of the invention is that the light corresponding to a focal point of order higher than +1 (if n=1) of the second partial profile is not lost, but contributes to the focal point for near vision.

In a preferred embodiment, n=1 and the second partial diffractive profile of the IOL has
  a focal point of order +2 that coincides with the diffractive focal point for intermediate vision, and
  a focal point of order +3 that coincides with the diffractive focal point for near vision.

According to preferred embodiment, the step heights of the first and second partial diffractive profiles fulfill the following condition in at least a portion of said diffractive profile: $a_2 > a_1$.

In a preferred embodiment, n=1 and the step heights of the first and second partial diffractive profiles 26, 28 fulfill the following conditions in at least a portion of said diffractive profile 24: $0.5 < a_1 < 1$, preferably $0.5 < a_1 < 0.7$, and most preferably $0.53 < a_1 < 0.62$; and $0.5 < a_2 < 1$, preferably $0.6 < a_2 < 0.9$, and most preferably $0.7 < a_2 < 0.8$. If n=2, the step heights fulfill the conditions $2 < a_1 + a_2 < 3$, as stated above, and further $1 < a_1 < 1.5$ and $1 < a_2 < 1.5$.

In another preferred embodiment, the step heights $a_1$ of the first profile are <1, while the step heights $a_2$ of the second profile are >1. In a particularly preferable embodiment, the step heights of the first and second partial diffractive profiles fulfill the following conditions in at least a portion of said diffractive profile: $0.25 < a_1 < 0.45$, preferably $0.30 < a_1 < 0.40$, and most preferably $0.33 < a_1 < 0.37$; and $1.20 < a_2 < 1.40$, preferably $1.25 < a_2 < 1.35$, and most preferably $1.28 < a_2 < 1.32$.

With this choice of parameters, the intensity at the diffractive focal point for intermediate vision can be increased, at the expense of the intensity of the diffractive focal point for near vision, which has been found preferable for some patients.

Preferably, the diffractive focal points for intermediate vision and for far vision are located on the optical axis at a distance corresponding to between +0.5 and +1.5 dioptres. In addition or alternatively, the diffractive focal points for near vision and for far vision are located on the optical axis at a distance corresponding to between +1.5 and +2.5 dioptres.

Particularly in embodiments, where $a_1 < 1$ and $a_2 > 1$, the diffractive focal points for intermediate vision and for far vision are in some embodiments located on the optical axis at a distance corresponding to between +1.5 and +2.0 dioptres, and in particular at a distance corresponding to +1.75 dioptres. In addition or alternatively, the diffractive focal points for near vision and for far vision are located on the optical axis at a distance corresponding to between +3.0 and +4.0 dioptres, and in particular at a distance corresponding to +3.5 dioptres.

At a pupil size of 4.5 mm and with green light at a wavelength of 543 nm, the modulation transfer function (MTF) for the IOL according to a preferred embodiment at 50 cycles/mm as a function of position on the optical axis displays distinguishable peaks corresponding to the diffractive focal points for far, intermediate and near vision. In other words, according to this embodiment, the "trifocal nature" of the IOL is exhibited in distinguishable MTF-peaks on the optical axis, provided that the pupil aperture is large enough. As will be seen with reference to specific embodiments below, for smaller pupil apertures, the peaks can merge in the MTF-diagram, such that they are no longer distinguishable in the MTF-diagram. According to preferred embodiments, a focal point is characterized by a MTF at 50 cycles/mm of 0.1 or more, preferably 0.15 or more.

Preferably, at a pupil size of 4.5 mm, 50 cycles/mm and with green light at a wavelength of 543 nm,
  the MTF value corresponding to the focal point for near vision is larger than the MTF value corresponding to the focal point for intermediate vision, and/or
  the MTF value corresponding to the focal point for far vision is larger than the MTF value corresponding to the focal point for near vision.

According to this embodiment, the far vision is given priority at large pupil sizes, which occur under weak light conditions. In addition or alternatively, at a pupil size of 2.0 mm, 50 cycles/mm and with green light at a wavelength of 543 nm, the MTF value corresponding to the focal point for near vision is larger than the MTF value corresponding to the focal point for far vision. According to this embodiment, at low pupil apertures of for example 2.0 mm, the focal point for near vision is given priority. This is advantageous, because near vision is usually needed at good light conditions, for example when reading a book. Note that in ordinary IOLs, including the IOL of WO'169, the distribution of light among the focal points is largely independent of the pupil aperture. As will become apparent from the description of specific embodiments below, with the IOL of the invention, it is possible to provide for strongly aperture dependent distributions of light, allowing for a large fraction of light to be focused to the focal point for far vision at large pupil sizes (corresponding to low light conditions) and a considerably smaller fraction of light focused to said focal point for far vision at small pupil sizes (corresponding to good light conditions), to the benefit of the intensity at the focal points for intermediate and near vision.

In alternative embodiments, at a pupil size of 4.5 mm, 50 cycles/mm and with green light at a wavelength of 543 nm,
  the MTF value corresponding to the focal point for near vision is lower than the MTF value corresponding to the focal point for intermediate vision.

This has been found particularly useful in cases where $a_1 < 1$ and $a_2 > 1$.

At a pupil size of 2.0 mm, 50 cycles/mm and with green light at a wavelength of 543 nm, the MTF as a function of position on the optical axis preferably stays constantly above 0.13, preferably constantly above 0.2 in a range extending from the diffractive focal point for near vision to the diffractive focal point for far vision. This allows for good vision over an extended focal range. As the skilled person will appreciate, the MTF can be measured according to Annex C of ISO 11979-2 guidelines: Ophthalmic implants—

Intraocular lenses part 2: optical properties and test methods in the version valid at the priority date.

In a preferred embodiment,
a first extended depth of focus is defined as the difference between the focal powers of the diffractive focal points for near vision and far vision, and
a second extended depth of focus is defined as the difference between the focal powers of the diffractive focal points for intermediate vision and far vision,
and the first extended depth of focus is an integer multiple of the second extended depth of focus, and in particular by a factor of 2 or 3.

In a preferred embodiment, the diffractive profile has non-vertical steps having a width of between 4 μm and 100 μm, in particular between 10 μm and 50 μm. In addition or alternatively, the diffractive profile has rounded edges with a minimum radius of curvature of 0.1 μm or more at the top of the step. Accordingly, in the preferred embodiments, the diffractive profile does not correspond to a conventional sawtooth-like structure with vertical steps and sharp edges, but is smoothed for better optical performance Such smoothing can be mathematically described by a convolution of a sharp sawtooth structure with a suitable smoothing function, which is also referred to as a "mollifier" in the art.

In a preferred embodiment,
the first partial diffractive profile has step positions centered at radial positions $r_n$ with respect to the optical axis located at $r_n = \sqrt{2n \cdot \lambda \cdot F_1}$, or centered at radial positions that on average deviate from these locations by less than 5%, preferably less than 1%, and the second partial diffractive profile has step positions centered at radial positions at $r_n = \sqrt{2n \cdot \lambda \cdot F_2}$, or centered at radial positions that on average deviate from these locations by less than 5%, preferably less than 1%, wherein
n is the number of the steps counted from the center of the profile,
$F_1$ is the focal length of the diffractive focal point of order +1 of the first partial diffractive profile,
$F_2$ is the focal length of the diffractive focal point of order +1 of the second partial diffractive profile,
and wherein $F_2$ is an integer multiple of $F_1$, where in particular, $F_2 = 2 \cdot F_1$ or $F_2 = 3 \cdot F_1$.

In a preferred embodiment, the IOL has a lens body, and the optical axis is decentered with regard to a geometric center of the IOL lens body.

Preferably, the IOL of the invention is further configured for compensating at least partially for ocular spherical aberration, ocular chromatic aberration, and/or for providing an extended range of vision.

BRIEF DESCRIPTION OF THE DRAWINGS

FIG. 4c is a close-up view of the first two steps of the profile of FIG. 3, in which a smoothening using a convolution with a Gaussian mollifier with two exemplary variances is shown, FIG. 5a shows the MTF at 50 cycles/mm as a function of diffractive power and for different pupil apertures for a trifocal IOL of the invention, FIG. 5b shows the MTF at 50 cycles/mm as a function of diffractive power and for different pupil apertures for a trifocal IOL according to prior art, FIG. 7 shows the longitudinal chromatic aberration (LCA) at the focal points for far, intermediate and near vision for two trifocal IOLs according to prior art and two trifocal IOL's according to the invention, wherein in each case, one of the IOLs is made from PMMA and one IOL is made from the applicants proprietary hydrophobic acrylic material GF as described in WO 2006/063994 A1.

DETAILED DESCRIPTION

Figure 1:
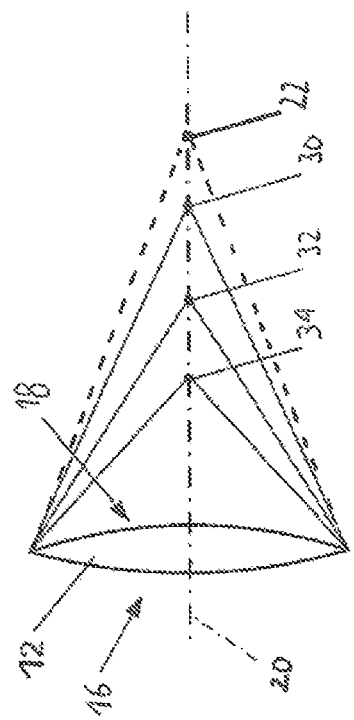
FIG. 1 is a schematic plan view of an IOL according to an embodiment of the invention.

For the purposes of promoting an understanding of the principles of the invention, reference will now be made to a preferred embodiment illustrated in the drawings, and specific language will be used to describe the same. It will nevertheless be understood that no limitation of the scope of the invention is thereby intended, such alterations and further modifications in the illustrated IOL and such further applications of the principles of the invention as illustrated therein being contemplated as would normally occur now or in the future to one skilled in the art to which the invention relates.

The term "near vision" as used herein may e.g. correspond to vision provided when objects at a distance from the subject eye of between about 30 cm to 60 cm are substantially in focus on the retina of the eye.

The term "far vision" may correspond to vision provided when objects at a distance of at least about 180 cm or greater are substantially in focus on the retina of the eye.

The term "intermediate vision" may correspond to vision provided when objects at a distance of about 60 cm to about 150 cm from the subject eye are substantially in focus on the retina of the eye. Note also that predicting the most appropriate IOL power for implantation has limited accuracy, and an inappropriate IOL power can leave patients with what is referred to in the art as "residual refraction" following surgery. Accordingly, it may sometimes be necessary for a patient who has received an IOL implant to also wear spectacles to achieve good far vision.

Figure 2:
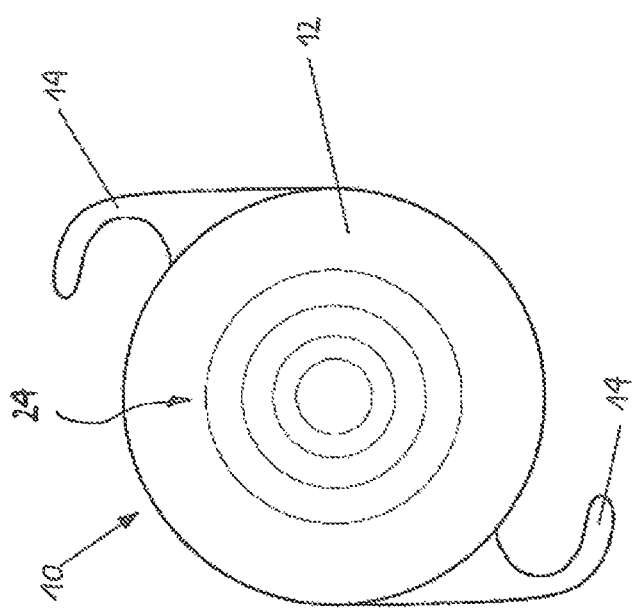
FIG. 2 is a schematic sectional view of the IOL according to FIG. 1, where diffractive focal points for near, intermediate and far vision, as well as a virtual respective focal point are shown.

A general configuration of an intraocular lens 10 according to an embodiment of the invention is illustrated in FIGS. 1 and 2. As may be seen in these figures, the lens includes a central optical body 12 and, in this exemplary configuration, two flexible supports 14, so-called "haptics" (not shown in FIG. 2), on the outer edge of the lens 10 in order to support it in the capsular bag when it is implanted in the eye of a patient. However, other alternative configurations are known to one skilled in the art and applicable in an intraocular lens according to the invention, such as for example a larger number of haptics, loop-shaped haptics, etc.

The intraocular lens 10 according to the illustrated embodiment of the invention is a lens of the diffractive type. The central optical body 12 includes an anterior face 16 and a posterior face 18, and has a substantially anteroposterior axis 20. The anterior and/or posterior faces 16, 18 have curvatures such that the lens 10 would direct a portion of the incident light onto a refractive focal point 22, or of "diffractive order zero", on the optical axis. In other words, without any diffractive profile on the anterior or posterior surface 16, 18, incoming light beams that propagate parallel to the optical axis 20 from the left in FIG. 2 would be focused at the refractive focal point 22. However, as will be explained in more detail below, with the specific choice of diffractive profiles according to the invention, only very little light is actually directed to the refractive focal point. Graphically speaking, in preferred embodiments of the present invention, the refractive focal point 22 is a "deactivated" or a "virtual focal point", which is indicated by the hatched lines in FIG. 2.

In the embodiment shown, the lens 10 has an asphericity with an aspherical aberration of −0.11 μm at an aperture or pupils size of 5.0 mm. This asphericity ensures a natural balance between the sensitivity to contrast and the field depth by inducing a moderate positive spherical aberration of the aphakic eye, the average spherical aberration of the human cornea being around +0.28 micrometers. In an alternative embodiment, the asphericity may be higher allowing to compensate for the cornea aberration to a higher degree. This would allow for an even better image quality, albeit at the price of making the optical performance of the lens more sensitive toward lens decentration and tilt within the eye.

Figure 3:
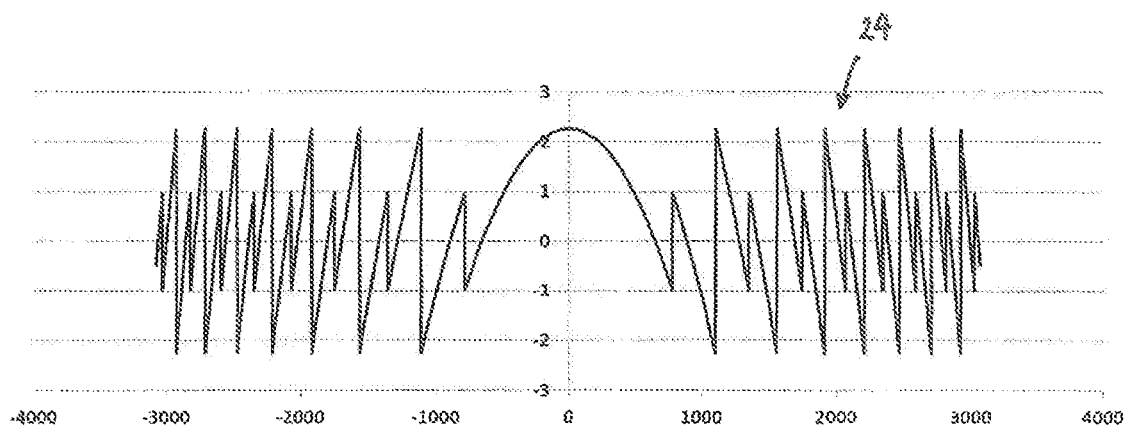
FIG. 3 is a schematic view of the diffractive profile for an IOL of the invention that can be generated by a superposition of the first and second partial profiles shown in FIGS. 4a and 4b.
Figure 4A:
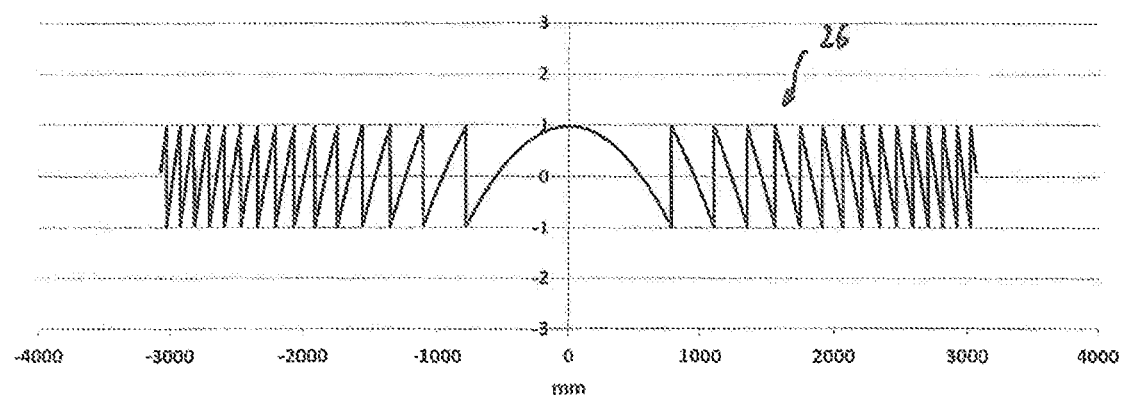
FIG. 4a is a schematic view of the first partial profile used in constructing the diffractive profile of FIG. 3.
Figure 4B:
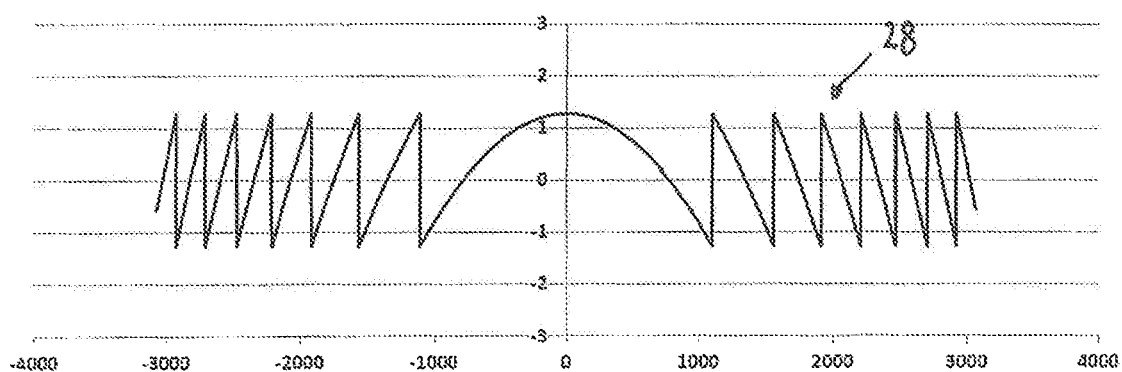
FIG. 4b is a schematic view of the second partial profile used in constructing the diffractive profile of FIG. 3.

On its anterior face 16, the lens 10 has a relief 24 resembling a diffractive profile, which is only schematically indicated in FIG. 1. The diffractive profile 24 is illustrated in FIG. 3 and formed by the superposition of a first diffractive profile 26, illustrated in FIG. 4a, and a second diffractive profile 28, illustrated in FIG. 4b. In FIGS. 3, 4a and 4b, all units on both axes are in μm. Accordingly, it is seen that in these figures, the height of the profiles is considerably exaggerated with respect to the radial distance r from the optical axis 20.

The first diffractive profile 26 is a profile of the kinoform type, approximately fitting the function:

$$H_1(r) = a_1\left(1 - \frac{r^3}{R^3}\right)\frac{\lambda}{2\pi}\left(\frac{1}{n_2 - n_1}\right)\left(\text{mod}\left[\left[F_1 - \sqrt{r^2 + F_1^2}\right]2\frac{\pi}{\lambda}, 2\pi\right] + \pi\right) \quad \text{Eq. 1}$$

The term "kinoform profile" is e.g. explained in "Diffractive Optics-Design, Fabrication and Test" by Donald O'Shea et al., SPIE tutorial texts; TT62 (2004), and refers to diffractive optical elements whose phase-controlling surfaces are smoothly varying. This is different from so-called "binary optical elements" with a discrete number of phase-controlling surfaces, e.g. surfaces introducing a zero and a π phase difference on the incident wavefront. In this equation, $H_1(r)$ is the height of the first partial diffractive profile 26, as a function of the radial distance r relatively to the optical axis, R is the radial distance from the outer edge of the lens to the optical axis, λ, is the wavelength at which the eye has greatest sensitivity (normally 550 nm), $n_2$ and $n_1$ are refractive indexes of the material of the lens and of its implantation medium, $a_1$ is an amplitude parameter (0.57 in the illustrated embodiment), and $F_1$ is the focal length of the focal point of order +1 of this first partial diffractive profile 26 (555 mm for +1.8 diopters in this embodiment).

The second partial diffractive profile 28 is also a profile of the kinoform type, approximately fitting the function:

$$H_2(r) = a_2\left(1 - \frac{r^3}{R^3}\right)\frac{\lambda}{2\pi}\left(\frac{1}{n_2 - n_1}\right)\left(\text{mod}\left[\left[F_2 - \sqrt{r^2 + F_2^2}\right]2\frac{\pi}{\lambda}, 2\pi\right] + \pi\right) \quad \text{Eq. 2}$$

In this equation $H_2(r)$ is the height of the second diffractive profile 28, as a function of the radial distance r with respect to the optical axis, $a_2$ is an amplitude parameter (0.74 in the illustrated embodiment) and $F_2$ is the focal length of the focal point of order +1 of this second partial diffractive profile 28 (1110 mm for +0.9 diopters in this embodiment).

While equations 1 and 2 define first and second partial profiles 26, 28 having vertical steps and sharp edges defined by the modulo function, the edges of the actual profiles will be rounded, and the steps would be inclined rather than vertical. A suitable shape of the first and second partial profiles 26, 28 can be obtained by a convolution of the above profile functions $H_1(r)$ and $H_2(r)$ with a corresponding smoothening function, which is referred to as a "mollifier" in the art. There is a variety of suitable mollifiers that would lead to a desired smoothening or rounding of the sharp edges and inclination of the steps. In fact, as the skilled person will appreciate, any convolution will lead to a rounding of sharp edges and inclination of vertical steps of a step function.

In a preferred embodiment, the mollifier M(r) can be represented by a Gaussian function as follows:

$$M(r) = \frac{1}{\sqrt{2\pi\sigma^2}}\exp\left\{-\frac{r^2}{2\sigma^2}\right\}$$

The convolution of the profile function H(r) and the mollifier M(r) is defined in the usual manner as:

$$H*M = \int H(x)M(r-x)dx$$

FIG. 4c shows the results of the convolution of the combined profile H(r) (see equation 3 below) with the mollifier M(r), where the variance $\sigma^2$ is expressed in terms of a convolution parameter "conv", which has the unit micrometers, as follows:

$$\sigma^2 = conv^2 \cdot \frac{1}{8 \cdot 10^6 \cdot |\ln(0.5)|}$$

In FIG. 4c, examples of the result of the convolution for three values of conv, namely conv=0 μm, 25 μm and 50 μm, are shown. For conv=0 μm, the mollifier M(r) corresponds to the Dirac delta function, which leaves the original profile H(r) unaffected. For increasing values of cony, the edges of the steps are increasingly rounded, and the inclination of the originally vertical steps increases.

Note that the rounding of the sharp profile steps by means of a convolution is already described in the aforementioned previous application WO'169, where the inclined steps and round edges can also be seen in FIGS. 3, 4a and 4b.

The relief or "profile" 24 resulting from the superposition of both of these partial profiles 26, 28 therefore approximately fits the formula: Eq. 3:

$$H(r)=H_1(r)+H_2(r),$$

as illustrated in FIG. 3. In this embodiment $F_2=2 \cdot F_1$, which means that every second step position of the first partial profile 26 coincides with a step of the second partial profile 28, or, in other words, that the second diffractive profile has an average spatial frequency half of the one of the first diffractive profile. The combined profile 24 therefore has large steps, resulting from the addition of a step of the first partial profile 26 with a step of the second partial profile 28, alternating with small steps, corresponding to one step out of two of the first partial profile 26.

Note that in the case where the profiles are not apodized, the factor $(1-r^3/R^3)$ in equations 1 and 2 is simply 1, as is the case in the embodiment shown herein.

Further, in this way the focal point of order +2 of the second partial profile 28 coincides on the optical axis 20 with the focal point of order +1 of the first partial profile 26.

In the embodiment shown in FIGS. 3, 4a and 4b, $a_1$ is 0.57, and $a_2$ is 0.74. This is very different from the embodiment shown e.g. in WO'169, where $a_1$=0.44 and $a_2$=0.27. This different choice of amplitudes leads to an entirely different optical behavior. In fact, it is seen that the IOL 10 has

- a focal point for far vision 30 (see FIG. 2) that coincides with the focal point of order +1 of the second partial diffractive profile 28,
- a focal point 32 for intermediate vision that coincides with the focal point of order +2 of the second partial diffractive profile 28, and also with the focal point of order +1 of the first partial diffractive profile 26, and
- a focal point for near vision 34 that coincides with the focal point of order +3 of the second partial diffractive profile 28.

In an alternative embodiment, the steps of the second partial profile 28 could coincide with every third step of the first partial profile 26, in which case the diffractive focal point of order +1 of the first partial profile 26 would coincide with and contribute to the focal point for near vision 34.

In the embodiment shown, only a negligible amount of light is focused on a position on the optical axis 20 that would correspond to the refractive focal point 22, or, in other words, the diffractive focal point of order 0.

It should be appreciated that the first and second partial profiles 26, 28 are in a sense only virtual or "auxiliary" profiles that mainly serve to construct the "total profile" 24. In particular, it is not per se clear that a given focal point of a partial profile will also be present in the diffraction pattern of the total, combined profile. However, it is seen that if the coefficients $a_1$ and $a_2$ are properly chosen, the total profile 24 does exhibit diffractive focal points that can in fact be attributed to the diffractive focal points of the individual partial profiles 26, 28. Further, by properly choosing the factors $a_1$ and $a_2$, a distribution of energy between the different focal points of the total profile 24 can be partitioned in a very useful way, as will be demonstrated below.

The inventors have found out that in embodiments of the present invention, the percentage of light directed to the focal point 34 for near vision depends in good approximation on the sum of $a_1$ and $a_2$, while the ratio of the percentage of light directed to the intermediate vision focal point 32 over the percentage of light directed to the far vision focal point 30 is essentially governed by the ratio $a_1/a_2$. Further, the inventors could derive empiric equations for estimating the light partition between the three focal points for near, intermediate and far vision as follows:

% Near=20*[($a_1+a_2$)EXP(2*($a_1+a_2$)/1.5)]  Eq. 4

% Inter/% Far=1*[($a_1/a_2$)EXP(2*($a_1/a_2$))]  Eq. 5

% Far=[100−Eq4]/[1+Eq5]  Eq. 6

% Inter=100−Eq6−Eq4  Eq. 7

Herein, "% Near", "% Inter" and "% Far" indicate the percentage of light energy directed to the respective focal point 34, 32, 30 for the near, intermediate and far vision, where the three percentages are chosen such as to add up to 100%. In other words, these equations only reflect the distribution of light between the respective focal points, but not the distribution of the light around the respective focal points.

The above equations 4-7 are found to give fairly good predictions of the actual distribution of light, provided that $1<a_1+a_2<2$ and $0.5<a_1<1$ and $0.5<a_2<1$.

A way of estimating the optical priority of an intraocular lens comprises determining experimentally its modulation transfer function (MTF). The MTF of an optical system can e.g. be measured according to annex C of ISO 11979-2 and reflects the proportion of the contrast which is transmitted through the optical system for a determined spatial frequency of a test pattern, which frequency is defined as "cycles/mm" or "lp/mm", "lp" denotes "line pairs". Generally, the contrast decreases with an increase in spatial frequency. As a first approximation, the percentage of light (E f %) directed to a given focal point is obtained from the MTF peak values at 50 cycles/mm according to the following equation:

% Ef=MTF peak/(MTF far+MTF inter+MTF near)*100,  Eq. 8 with f denoting one of the far, the intermediate or the near focal point.

In FIG. 5a, MTF curves of the trifocal lens 10 according to an embodiment of the invention versus the focal power in dioptres are shown for different pupil apertures in an eye model according to the ISO 1 standard, at 50 cycles/mm and with monofocal green light (543 nm). The dotted curve corresponds to a pupil size of 4.5 mm and shows three peaks corresponding to the focal point for far vision at 18.25 dpt, to the focal point for intermediate vision at 19.15 dpt and to the focal point for near vision at 20.05 dpt, respectively. The spacing in dioptres (dpt) between two consecutives MTF peaks is 0.9 dpt, thus corresponding to two powers additions of +0.9 dpt and +1.8 dpt with respect to the far focus, respectively. For this lens at 4.5 mm aperture, the distribution of the light between the three focal points is 46.67% for far vision, 33.33% for near vision and 20% for intermediate vision.

This is in good agreement with the distribution of light according to equations 4, 6 and 7 above, which would yield a distribution of 45.06% for far vision, 22.89% for intermediate vision and 32.05% for near vision. Accordingly, it is seen that the empiric equations 4 to 7 capture the distribution of light among the focal points quite well.

It is further seen in FIG. 5a that for a pupil aperture of 4.5 mm, rather little light is directed elsewhere than on these three focal points, and in particular that little light is directed to the position at 17.35 dpt corresponding to the refractive or "zero order" focal point, which is indicated in FIG. 5a for illustration purposes only. It is therefore seen that the zero order focal point is only a "virtual focal point" or "deactivated".

FIG. 5a further shows the MTF curve at 50 cycles/mm for a pupil aperture of 3.75 mm in the chain-dotted line, for a pupil aperture of 3.0 mm in the solid line and for a pupil aperture of 2.0 mm in the dashed line. As can be seen from FIG. 5a, by decreasing the pupil aperture from 4.5 mm to 3.0 mm, the MTF peaks for near and intermediate vision merge into a broader single peak, so that at these small pupil apertures, the IOL essentially becomes bifocal. By further constricting the pupil aperture to 2.0 mm, the two residual MTF peaks give rise to a single very broad and very high peak. This can be attributed at least partly to the well-known "pinhole" diffraction, which becomes more significant at small apertures, wherein the light wavefront is then affected to a larger degree by the edges of the hole.

It is worth noting that this pin-hole diffraction contributes to an extended depth of focus, i.e. for smaller pupil apertures, the MTF drops increasingly less between the focal points. At a pupil aperture as low as 2.0 mm, the pin-hole effect is maximized, and the MTF stays above 0.2 in the entire range between 18 dpt and 20.5 dpt, i.e. throughout the entire range from near to far vision. It is further seen that at small pupil sizes such as 2.0 mm, the MTF at 18.25 dpt (far vision) drops considerably, while the MTF at near and intermediate vision (20.05 dpt and 19.15 dpt) dramatically increase. This is also seen in FIG. 6a, where the percentage of light directed to any given focal point of the IOL according to the embodiment of the invention is shown as a function of pupil aperture, where the percentage of light is related with the MTF in the way defined in equation 8 above.

Figure 6A:
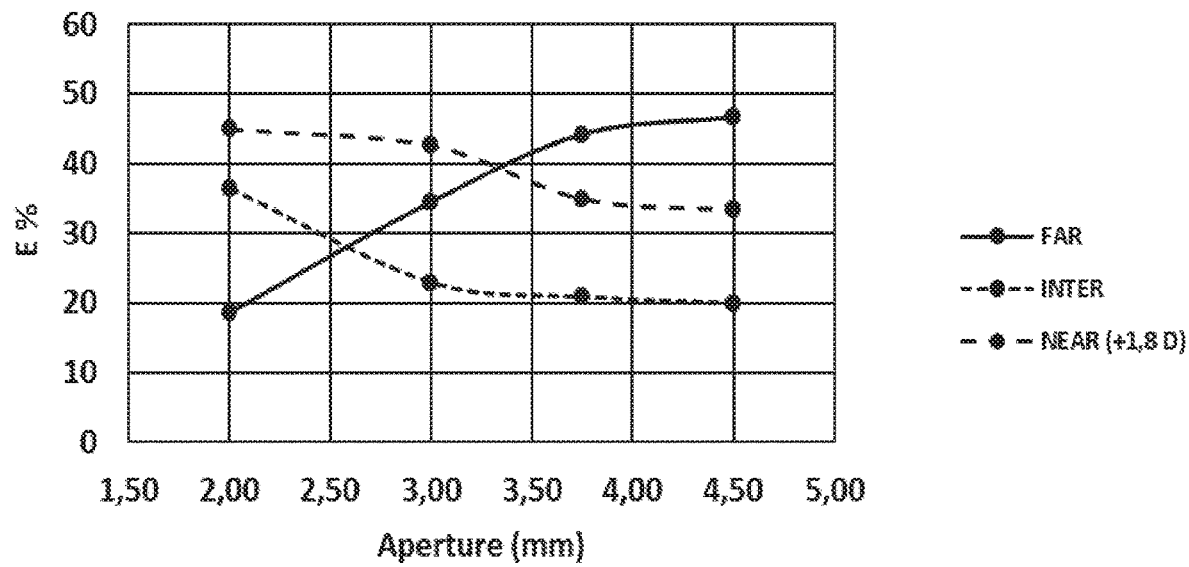
FIG. 6a shows the distribution of light energy among the focal points for far, intermediate and near vision as a function of pupil aperture for the trifocal IOL according to an embodiment of the invention.

As is seen in FIG. 6a, for large pupil apertures (4.5 mm), the fraction of light directed to the focal point for far vision exceeds the fractions for near and intermediate vision, while with decreasing aperture, the fraction of light directed to the focal points for near and intermediate vision increases, while the fraction of light directed to the focal point for far vision decreases, and in fact drops below that of the other two focal points. This behavior is unusual for trifocal IOLs, but in fact highly advantageous, because far vision is often needed under poor light conditions, where the pupil size tends to be large due to the natural pupil accommodation reflex, while near and intermediate vision are typically needed under good light conditions, for example when reading a book or working on a computer. The IOL according to preferred embodiments of the invention hence meets both demands extremely well. In particular, providing more light at the focal point for far vision than for near and intermediate vision under poor light conditions, should improve the image quality by limiting photic phenomena, such as halos, under large pupil apertures and mesopic conditions, the out of focus and closer images being less intense.

Figure 6B:
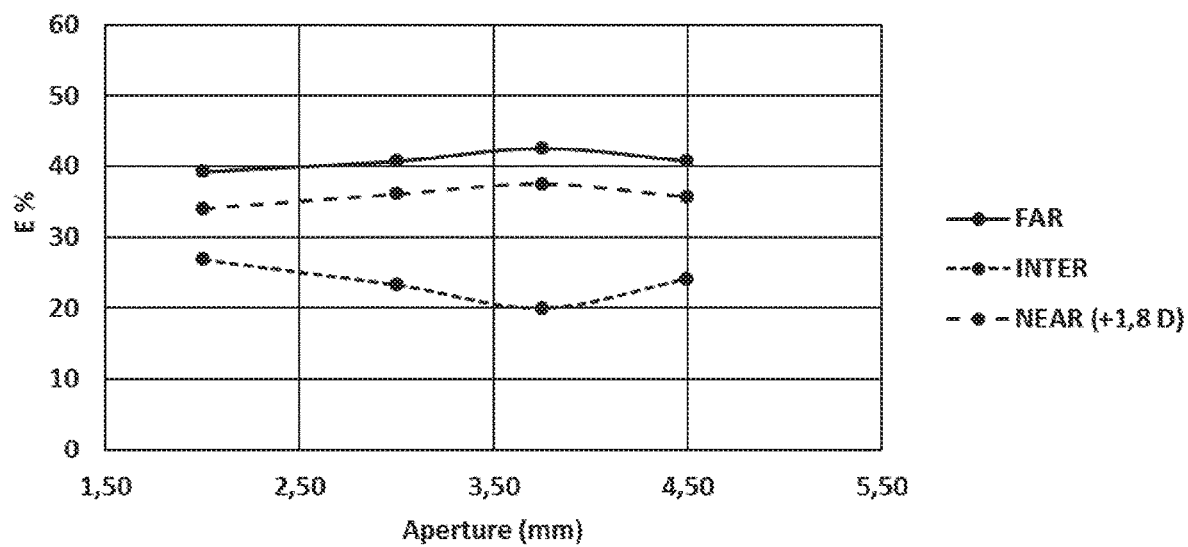
FIG. 6b shows the distribution of light energy among the focal points for far, intermediate and near vision as a function of pupil aperture for the trifocal IOL according to prior art.

The behavior of the IOL of the invention shall be compared with that of the trifocal IOL of WO'169, where the MTF is shown for comparison in FIG. 5b, and the distribution of light energy among the respective focal points is shown in FIG. 6b. Note that in the embodiment according to WO'169, apodisation was used. As can be seen from FIG. 5b, similar to the IOL of the invention, the peaks corresponding to the focal points for near and intermediate vision merge when the pupil size decreases from 4.5 mm to 3.0 mm, and the depth of focus increases. However, unlike the IOL of the invention, in the prior art trifocal lens of WO'169, without apodisation the relative distribution of light among the three focal points is approximately independent of the pupil size (see FIG. 6b). Accordingly, this prior art IOL without apodisation does not allow the far vision being dominant at low light conditions (large pupil apertures) and the near vision being dominant at good light conditions (small pupil apertures) in the same lens.

A further advantage of the trifocal IOL 10 of the invention is that it allows to diminish or correct longitudinal chromatic aberration (LCA). FIG. 7 shows the longitudinal chromatic aberration (LCA) at the focal points for far, intermediate and near vision for two IOLs according to the invention and two IOLs according to WO'169. Herein, "LCAf" denotes the longitudinal chromatic aberration at a given focal point (f), where "f" represents a respective one of the focal points (i.e. far, intermediate or near vision). Each of these focal points corresponds to an additional optical power as compared to the focal point for far vision in diopters, which are indicated on the horizontal axis of FIG. 7. Accordingly, in the exemplary embodiment, focal points for far vision correspond to 0 dpt, focal points for intermediate vision correspond to 0.9 dpt and focal points for near vision correspond to 1.8 dpt on the horizontal axis of FIG. 7.

The numeric value of LCAf is obtained by the shift of the MTF-peak measured on an optical bench at 50 cycles/mm and a pupil aperture of 4.5 mm, expressed in diopters, when the light changes from monochromatic red (650 nm) to monochromatic blue (480 nm). This shift can be measured for each of the three MTF-peaks corresponding to the three focal points, and the results are shown in FIG. 7.

In FIG. 7, the solid lines indicate the values of LCAf for two IOLs according to WO'169 made from different materials, namely PMMA (cross symbol) and GF (dots), where GF is a proprietary hydrophobic acrylic material of the present applicant as disclosed in WO2006/063994 A1. The Abbe numbers of PMMA and GF are 53.23 and 42.99, respectively. The Abbe number is a measure of the material's dispersion, i.e. the variation of its refractive index with wavelength, where high values indicate low dispersion. In the trifocal lenses of WO'169, the focal point for far vision (0 dpt in FIG. 7) is a purely refractive focal point. At 0 dpt, both of the prior art trifocal lenses show a positive value for LCAf, amounting to 0.3 dpt in case of PMMA and 0.65 dpt in case of GF. A positive value of LCAf is expected, because for these materials, the index of refraction increases with decreasing wavelength, so that the refractive optical power for blue light is larger than the refractive optical power for red light. Moreover, a higher value for LCAf is found for the GF-lens as compared to the PMMA-lens, due to its smaller Abbe number.

In the prior art IOLs of WO'169, the focal point for near vision (at 1.8 dpt) corresponds to the diffractive focal point of order +1 of a first partial diffractive profile, to which a contribution of the focal point of order +2 of a second partial diffractive profile is added. The focal point for the intermediate vision (at 0.9 dpt) corresponds to the diffractive focal point of order +1 of the second partial diffractive profile. As was explained in the summary of the invention, the LCA for diffractive focal points is "negative" in the sense that the diffractive optical power increases with increasing wavelength. Accordingly, the negative LCA at the diffractive focal points lowers the total LCAf at the focal points for intermediate vision to 0.05 (PMMA) and 0.40 (GF), and even further lowers the total LCAf at the focal points for near vision to 0.08 (PMMA) and 0.15 (GF).

Further shown in FIG. 7 with broken lines are the values for LCAf for two IOLs according to the invention, where the cross-symbols again represent an embodiment based on PMMA and the dot-symbols represent an embodiment in GF. As can be seen in FIG. 7, for the IOL of invention, the LCAf curves are vertically shifted to lower values as compared to the respective prior art IOL made of the same material. In particular, for the focal points for far vision (0 dpt), the value LCAf for the GF-lens is lowered to 0.4 diopters and the LCAf value for the PMMA lens is lowered to −0.03 dpt, which means that there is practically no longitudinal chromatic aberration for the focal point for far vision in this PMMA-based embodiment of the invention.

The reason why the LCA at the focal point for far vision is reduced as compared to the prior art trifocal lens of WO'169 is that according to the invention, the focal point for far vision is a diffractive focal point, namely a focal point of order +1 of the second partial profile, which therefore provides for a negative LCA, that compensates at least partially the positive LCA due to the refractive power of the lens. It is therefore seen that particularly if the GF material is to be used, the trifocal lens of the invention is clearly favorable with regard to LCA as compared to the prior art trifocal lens of WO'169.

As regards the prior art IOL based on PMMA, the average value of LCAf is already quite low, with moderately positive values at the focal point for far vision, moderately negative values at the focal point for near vision and almost vanishing longitudinal chromatic aberration at the focal point for intermediate vision. In fact, the LCA of the prior art PMMA trifocal lens is similar to that of the trifocal lens of the invention based on GF. The PMMA-version of the trifocal IOL of the invention has the benefit of vanishing LCA for far vision, although at the price of a more negative LCA of −0.7 dpt at the focal point for near vision. Negative values of LCAf for near vision can even be favorable for correcting the aphakic eye LCA, i.e. cornea LCA.

Trifocal IOLs are supposed to lead to an extended range of vision (EROV), from far vision (e.g. +0 dpt) to near vision (e.g. +1.8 dpt), without a discontinuity or significant gap of vision for the intermediate distance. From the MTF diagrams of FIGS. 5a and 5b, it is seen that such an EROV is indeed obtainable with the trifocal lenses of the invention as well as with the IOLs of WO'169. The EROV performance of a lens can be assessed under vital conditions in a more direct way by capturing the USAF targets by "defocusing" the target, i.e. by displacing the US target along the optical axis of the IOL while recording the object image. The applicant has systematically captured USAF-images for the IOL of the invention as well as the IOL of WO'169, for different wavelengths (green, red and blue) and for different pupil apertures (2.0, 3.0, 3.75 and 4.5 mm). It was confirmed that for monochromatic green light, both, the IOL of the invention as well as the IOL of WO'169 exhibit an EROV from 0 dpt to +2 dpt with constant image quality. In particular, both trifocal IOLs were superior to a commercially available bifocal IOL, which showed a degradation of the image quality between 0.75 dpt. and 1.25 dpt, especially for pupil apertures of more than 2.0 mm.

When the light source was changed from green light to red or blue light, it appeared that a commercially available diffractive bifocal lens with two diffractive focal points becomes essentially monofocal for far and near distance in the red and blue light, respectively, with corresponding image quality degradation at near and far distances, respectively. In contrast to this, the two trifocal IOLs according to WO'169 and according to the invention remain trifocal both in blue and red light, with a fully EROV from 0 dpt to 2.25 dpt, although the image quality is slightly affected at far distances for blue light and near distances for red light, as compared to the performance for green light.

Moreover, when comparing the USAF images of the IOL of the invention with those of the IOL according to WO'169, it is seen that the image quality for the IOL of the invention is superior for far vision at large pupil apertures (such as 4.5 mm), and for near vision at small pupil apertures, as was to be expected from the comparison of FIGS. 5a and 5b, and from the comparison of FIGS. 6a and 6b. Namely, as shown therein, the IOL of the invention favors near vision at small pupil apertures and far vision at large pupil apertures, in contrast to the IOL of WO'169, where the distribution of light among the focal points is largely independent of the pupil size.

Figure 8:
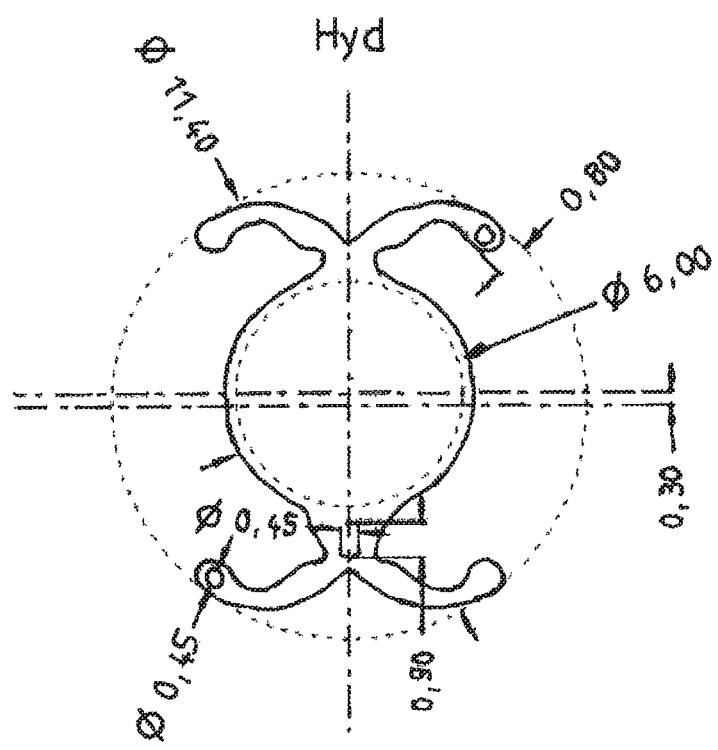
FIG. 8 is a plan view of an IOL according to an embodiment of the invention, with an asymmetric design having an optical portion that is off-centered by 0.3 mm with regard to the geometrical center of the IOL.

While longitudinal chromatic aberration of the eye can be corrected by an optical element with longitudinal chromatic aberration equal and opposite to that of the eye, alignment of such elements is critical, as otherwise an additional transverse chromatic aberration is induced, which is proportional to the decentration (see Zhang X, Bradley A, Thibos L N. Achromatizing the human eye: the problem of chromatic parallax. J Opt Soc Am, 1991; 8:686-91). However, the human pupil center is not located concentrically to the center of the capsular bag and it is not coaxial with the optical and visual axes In the vicinity of the visual axis, which joins the fixation point to the fovea by way of the nodal points, the correction of longitudinal chromatic aberration does not result in the induction of transverse chromatic aberration. In an embodiment, the haptics of the intraocular lens (IOL) optic can be advantageously designed to be asymmetrical, in order to allow the optical center of the IOL to be coincident with the presumed location of the visual axis, or the center of the entrance pupil. FIG. 8 is a schematic plan view of an IOL 10 according to an embodiment of the invention, in which the optical portion, i.e. the diffractive profile 24 is off-centered by 0.3 mm with regard to the outer diameter of the IOL.

Although the present invention has been described with reference to specific exemplary embodiments, it is obvious that modifications and changes may be carried out on these examples without modifying the general scope of the invention as defined by the claims.

For example, in alternative embodiments, an intraocular lens according to the invention may have different diffractive profiles, other than kinoforms, or exhibit different ratios between the periodicities and distances of the steps of the two superposed partial diffractive profiles. The partial diffractive profiles may also be superposed only on a portion of the anterior or posterior surface of the lens. The lens may also have different curvatures on its anterior and/or posterior faces, or no curvature, and these curvatures may, depending on the needs, either be aspherical or not. Moreover, other combinations of diffractive orders can be considered in order to achieve the three focal points, especially orders of 1 unit superior to those of the lens according to the invention described here above. In this particular case, the step height would obey the condition $2 < a_1 + a_2 < 3$.

Although a preferred exemplary embodiment is shown and specified in detail in the drawings and the preceding specification, these should be viewed as purely exemplary and not as limiting the invention. It is noted in this regard that only the preferred exemplary embodiment is shown and specified, and all variations and modifications should be protected that presently or in the future lie within the scope of protection of the invention as defined in the claims.

What is claimed is:

1. An intraocular lens, comprising:
   an anterior surface, a posterior surface and an optical axis, the lens being made of a material that has a refractive index;
   wherein at least one of the anterior or posterior surfaces has a diffractive profile formed thereon, the diffractive profile having:
   a diffractive focal point for far vision,
   a diffractive focal point for intermediate vision, and
   a diffractive focal point for near vision;

wherein the diffractive profile corresponds to a superposition of a first partial diffractive profile and a second partial diffractive profile;

the first partial diffractive profile has a focal point of order+n that coincides with either the diffractive focal point for intermediate vision or with the diffractive focal point for near vision;

the second partial diffractive profile has:
- a focal point of order+n that coincides with the diffractive focal point for far vision,
- a focal point of higher order than +n that coincides with the diffractive focal point for near vision;

wherein each of the first and second partial diffractive profiles has a plurality of steps with corresponding step heights;

wherein in at least a portion of the diffractive profile, the step heights are selected such that $n < a_1 + a_2 < n+1$, wherein:

$$a_1 = \overline{h_1} / \left( \frac{\lambda}{|n_2 - n_1|} \right),$$

$$a_2 = \overline{h_2} / \left( \frac{\lambda}{|n_2 - n_1|} \right),$$

$\overline{h_1}$ is the average of the step heights of the first partial diffractive profile in the portion of the diffractive profile, $\overline{h_2}$ is the average of the step heights of the second partial diffractive profile in the portion of the diffractive profile, $\lambda = 550$ nm, $n_2$ is the refractive index of the lens material, $n_1 = 1.3345$, and $n=1$ or $n=2$.

2. The intraocular lens of claim 1, wherein n=1, and wherein the second partial diffractive profile has:
a focal point of order+2 that coincides with the diffractive focal point for intermediate vision; and
a focal point of order+3 that coincides with the diffractive focal point for near vision.

3. The intraocular lens of claim 1, wherein the step heights of the first and second partial diffractive profiles fulfill the following condition in at least the portion of the diffractive profile: $a_2 > a_1$.

4. The intraocular lens of claim 1, wherein n=1, and wherein the step heights of the first and second partial diffractive profiles fulfill the following conditions in at least the portion of the diffractive profile: $0.5 < a_1 < 1$, and $0.5 < a_2 < 1$.

5. The intraocular lens of claim 1, wherein n=1, and wherein the step heights of the first and second partial diffractive profiles fulfill the following conditions in at least the portion of the diffractive profile: $0.5 < a_1 < 0.7$ and $0.6 < a_2 < 0.9$.

6. The intraocular lens of one of the preceding claims, wherein n=1, and wherein the step heights of the first and second partial diffractive profiles fulfill the following conditions in at least the portion of the diffractive profile: $0.53 < a_1 < 0.62$ and $0.7 < a_2 < 0.8$.

7. The intraocular lens of claim 1, wherein n=1 and the step heights $a_1$ of the first partial diffractive profile are <1, while the step heights $a_2$ of the second partial diffractive profile are >1.

8. The intraocular lens of claim 7, wherein the step heights of the first and second partial diffractive profiles fulfill the following conditions in at least the portion of the diffractive profile: $0.25 < a_1 < 0.45$ and $1.20 < a_2 < 1.40$.

9. The intraocular lens of claim 7, wherein the step heights of the first and second partial diffractive profiles fulfill the following conditions in at least the portion of the diffractive profile: $0.30 < a_1 < 0.40$ and $1.25 < a_2 < 1.35$.

10. The intraocular lens of claim 7, wherein the step heights of the first and second partial diffractive profiles fulfill the following conditions in at least the portion of the diffractive profile: $0.33 < a_1 < 0.37$ and $1.28 < a_2 < 1.32$.

11. The intraocular lens of claim 1, wherein the diffractive focal points for intermediate vision and for far vision are both located on the optical axis at a distance from each other corresponding to between +0.5 and +1.5 dioptres.

12. The intraocular lens of claim 1, wherein the diffractive focal points for near vision and for far vision are both located on the optical axis at a distance from each other corresponding to between +1.5 and +2.5 dioptres.

13. The intraocular lens of claim 1, wherein the diffractive focal points for intermediate vision and for far vision are both located on the optical axis at a distance from each other corresponding to between +1.5 and +2.0 dioptres.

14. The intraocular lens of claim 1, wherein the diffractive focal points for near vision and for far vision are both located on the optical axis at a distance from each other corresponding to between +3.0 and +4.0 dioptres.

15. The intraocular lens of claim 1, wherein at a pupil size of 4.5 mm and with green light at a wavelength of 543 nm, the modulation transfer function (MTF) at 50 cycles/mm as a function of position on the optical axis displays distinguishable peaks corresponding to the diffractive focal points for far, intermediate, and near vision.

16. The intraocular lens of claim 1, wherein at a pupil size of 4.5 mm, 50 cycles/mm and with green light at a wavelength of 543 nm, either the MTF value corresponding to the diffractive focal point for near vision is greater than the MTF value corresponding to the diffractive focal point for intermediate vision, or the MTF value corresponding to the diffractive focal point for near vision is less than the MTF value corresponding to the diffractive focal point for intermediate vision.

17. The intraocular lens of claim 16, wherein at a pupil size of 4.5 mm, 50 cycles/mm and with green light at a wavelength of 543 nm, the MTF value corresponding to the diffractive focal point for far vision is larger than the MTF value corresponding to the diffractive focal point for near vision.

18. The intraocular lens of claim 1, wherein at a pupil size of 2.0 mm, 50 cycles/mm and with green light at a wavelength of 543 nm, the MTF value corresponding to the diffractive focal point for near vision is larger than the MTF value corresponding to the diffractive focal point for far vision.

19. The intraocular lens of claim 1, wherein at a pupil size of 2.0 mm, 50 cycles/mm and with green light at a wavelength of 543 nm, the MTF as a function of position on the optical axis stays constantly above 0.13 in a range extending from the diffractive focal point for near vision to the diffractive focal point for far vision.

20. The intraocular lens of claim 1, wherein at a pupil size of 2.0 mm, 50 cycles/mm and with green light at a wavelength of 543 nm, the MTF as a function of position on the optical axis stays constantly above 0.2 in a range extending from the diffractive focal point for near vision to the diffractive focal point for far vision.

21. The intraocular lens of claim 1, wherein:
a first extended depth of focus is defined as the difference between a focal power of the diffractive focal point for near vision and a focal power of the diffractive focal point for far vision;
a second extended depth of focus is defined as the difference between a focal power of the diffractive focal point for intermediate vision and a focal power of the diffractive focal point for far vision; and
the first extended depth of focus is an integer multiple of the second extended depth of focus.

22. The intraocular lens of claim 21, wherein the first extended depth of focus is either two or three times the second extended depth of focus.

23. The intraocular lens of claim 1, wherein the diffractive profile has a plurality of non-vertical steps having a width between 4 μm and 100 μm.

24. The intraocular lens of claim 1, wherein the diffractive profile has a plurality of non-vertical steps having a width between 10 μm and 50 μm.

25. The intraocular lens of claim 1, wherein the diffractive profile has rounded edges with a radius of curvature of 0.1 μm or greater.

26. The intraocular lens of claim 1, wherein:
the steps of the first partial diffractive profile are centered with respect to the optical axis approximately at radial positions $r_n$ measured from the optical axis, the radial positions being: $r_n = \sqrt{2n \cdot \lambda \cdot F_1}$;
the steps of the second partial diffractive profile are centered with respect to the optical axis approximately at radial positions $r_n$ measured from the optical axis, the radial positions being: $r_n = \sqrt{2n \cdot \lambda \cdot F_2}$;
wherein:
n is the number corresponding to each step in the respective partial diffractive profile counted from the center of the profile,
$F_1$ is the focal length of the diffractive focal point of order+1 of the first partial diffractive profile,
$F_2$ is the focal length of the diffractive focal point of order+1 of the second partial diffractive profile,
and $F_2$ is an integer multiple of $F_1$.

27. The intraocular lens of claim 26, wherein $F_2 = 2 \cdot F_1$ or $F_2 = 3 \cdot F_1$.

28. The intraocular lens of claim 1, wherein:
the steps of the first partial diffractive profile are centered with respect to the optical axis within 5% of radial positions $r_n$ measured from the optical axis, the radial positions being: $r_n = \sqrt{2n \cdot \lambda \cdot F_1}$;
the steps of the second partial diffractive profile are centered with respect to the optical axis within 5% of radial positions $r_n$ measured from the optical axis, the radial positions being: $r_n = \sqrt{2n \cdot \lambda \cdot F_1}$;
wherein:
n is the number corresponding to each step in the respective partial diffractive profile counted from the center of the profile,
$F_1$ is the focal length of the diffractive focal point of order+1 of the first partial diffractive profile,
$F_2$ is the focal length of the diffractive focal point of order+1 of the second partial diffractive profile, and
$F_2$ is an integer multiple of $F_1$.

* * * * *